United States Patent [19]

Muldoon

[11] 4,229,968

[45] Oct. 28, 1980

[54] GAS MEASUREMENT AND ANALYSIS SYSTEM

[75] Inventor: James F. Muldoon, Neptune, N.J.

[73] Assignee: Electronic Associates, Inc., West Long Branch, N.J.

[21] Appl. No.: 946,784

[22] Filed: Sep. 28, 1978

[51] Int. Cl.³ .......................................... G01N 31/08
[52] U.S. Cl. ..................................... 73/23.1; 364/497
[58] Field of Search .................. 73/23, 23.1; 364/497, 364/582

[56] References Cited

U.S. PATENT DOCUMENTS

| | | | |
|---|---|---|---|
| 3,470,367 | 9/1969 | Frisby et al. | 73/23.1 |
| 3,721,813 | 3/1973 | Condon et al. | 73/23.1 |
| 3,732,466 | 5/1973 | Vesper et al. | 73/23.1 |
| 3,733,474 | 5/1973 | Edwards et al. | 73/23.1 |
| 3,751,966 | 8/1973 | Ryan et al. | 73/23.1 |
| 3,860,393 | 1/1975 | Campen | 73/23.1 |
| 3,863,489 | 2/1975 | Ayers et al. | 73/23.1 |
| 3,937,061 | 2/1976 | Rhodes | 73/23.1 |
| 4,002,052 | 1/1977 | Bordet et al. | 73/23.1 |
| 4,059,994 | 11/1977 | Annino et al. | 73/23.1 |
| 4,063,310 | 12/1977 | McDonald | 73/23.1 |

Primary Examiner—Stephen A. Kreitman
Attorney, Agent, or Firm—Allan Ratner

[57] ABSTRACT

A gas measurement and analysis system having a gas chromatograph which converts a gas mixture from a source to a time varying continuous signal. This signal is sampled and converted to digital form by an analog to digital converter which provides a stream of amplitude dependent digital values at equally spaced time intervals. These sampled signals are applied to a rate of change estimator system which provides an accurate estimate of the time derivative of the sampled signal by means of recursive digital feedback. The output of the estimator system is applied to a processor.

15 Claims, 9 Drawing Figures

GAS MEASUREMENT AND ANALYSIS SYSTEM

BACKGROUND OF THE INVENTION

A. Field of the Invention

This invention relates to the field of art of gas measurement and analysis systems and particularly with respect to gas chromatograph systems.

B. Prior Art

Prior system have been used to achieve an estimation of the rate of change of a noise-burdened signal particularly in the field of instrumentation electronics and radar signal processing. Such signals are characterized by having amplitudes which are of the same order as the noise. Many forms of differentiator networks associated with operational amplifiers exist each of which suffers in varying degrees from problems of extreme sensitivity, "hang-up" in the saturation mode and other undesirable nonlinear modes of operation in the presence of noise. Other prior systems have used filtering networks. However, filters have been limited because of size and weight. In addition, filters have provided undesirable varying amounts of amplitude and phase distortion of the original signal when the frequency content of the signal being processed is in the approximate spectral range of the noise being eliminated.

Additional prior art exists in the area of "off-line" processing techniques in which data points are collected which contain the processed signal imbedded in a noise component. Digital processing methods are used to separate the signal from the noise component by employing analytical methods such as the "least squares" technique. By means of such techniques, the primary trend of the desired function can be determined. However, such methods are normally limited by the excessive degree of computation time required and the necessity of operating in non-real time. Many operational systems require real time computational capability due to memory size limitations and limited processing power (in terms of time) of miniprocessor and microprocessor systems.

SUMMARY OF THE INVENTION

A system for measuring and analyzing a gas mixture which comprises a gas processor for producing a time varying signal which is related to the constituents of the gas mixture. A converter samples the time varying signal and converts it to digital form for providing a sampled data signal. A rate of change estimator provides a rate of change signal. The estimator includes recursive digital feedback means coupled to an output of the estimator and also to the converter. In this manner, there is produced past time value signals of the estimated rate of change signal and of the sampled data signal. The estimator further comprises means for combining the past time value signals with the sampled data signal for producing the estimated rate of change signal.

BRIEF DESCRIPTION OF THE DRAWINGS

FIGS. 3A–E are waveforms helpful in describing the operation of FIG. 1;

DETAILED DESCRIPTION

Figure 1:
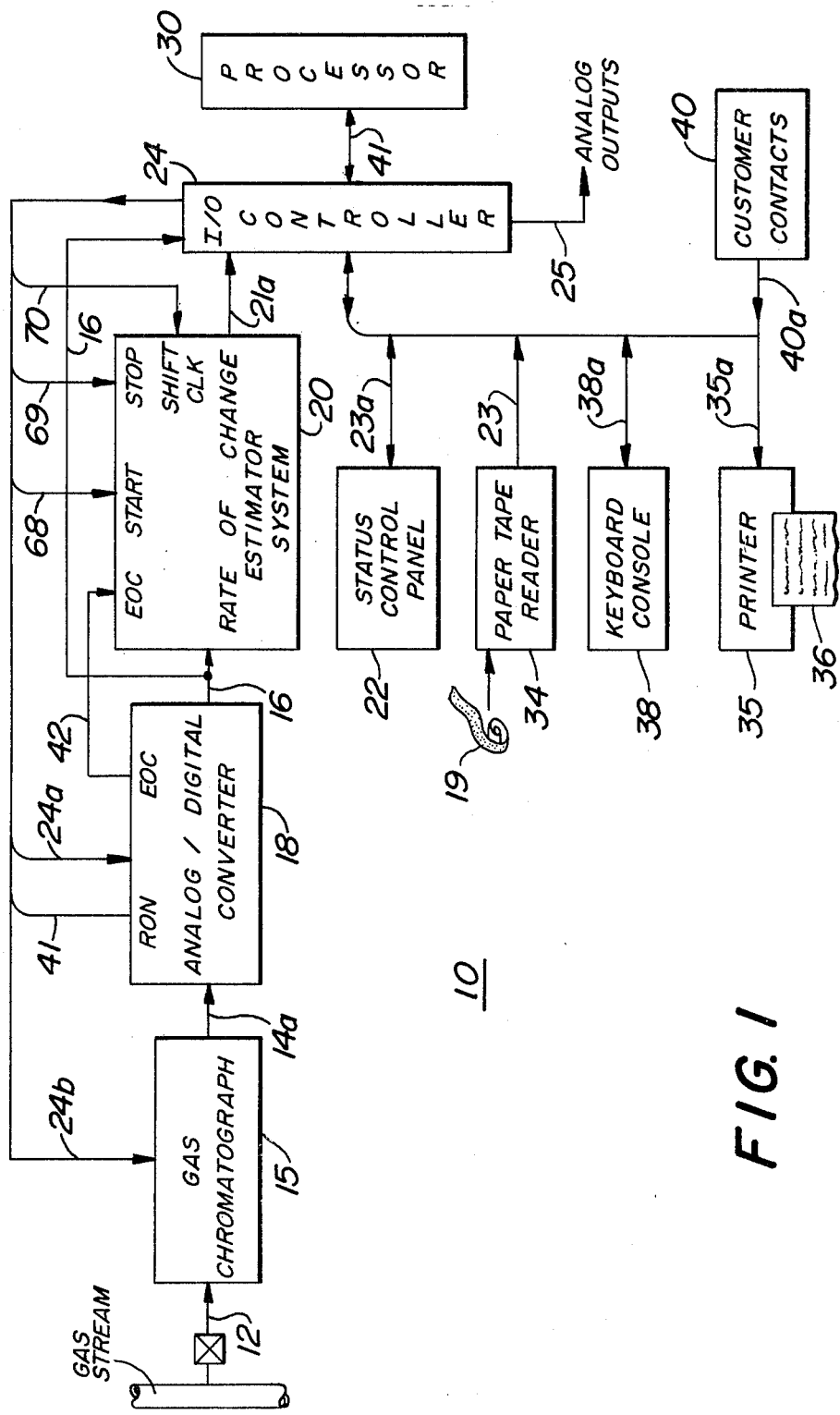
FIG. 1 is a block diagram of a gas chromatograph measurement and analysis system including a rate of change estimator system in accordance with the invention.
Figure 3A:
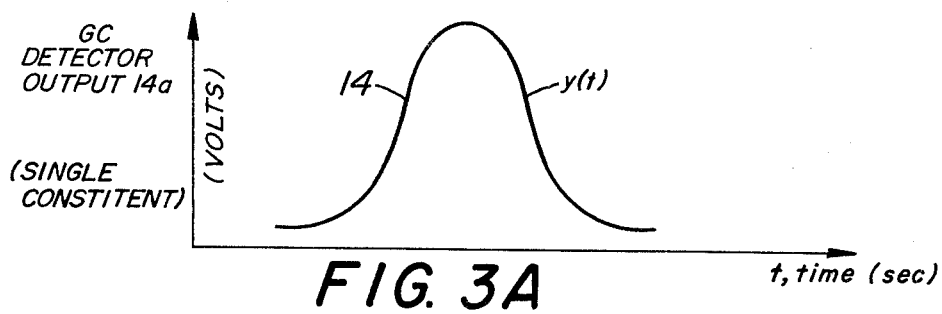

Referring to FIG. 1, there is shown a gas measurement and analysis system 10 which includes a gas chromatograph (GC). Chromatograph 15 converts a gas mixture from a source applied by way of input line 12 undergoing analysis to a time varying, continuous signal 14 (shown in FIGS. 3A, C) at GC detector output 14a. Signal 14 is sampled and converted to digital form by analog/digital converter 18 to provide a stream of amplitude dependent digital values (samples) 17 on line 16 (FIG. 3B) to a rate of change estimator system 20 and to processor 30. System 20 provides an accurate estimate at output 21a of the time derivative 21a of signal 14.

Using signal 21 and A/D output signal 17, processor 30 computes an accurate compositional analysis of the gas stream on line 12 currently under analysis. System 10 samples the gas stream, develops a GC output signal 14 and computes from the intelligence of this signal the composition of up to 15 gas constituents or components including noncombustibles, saturated and non-saturated hydrocarbons.

The computed output data 36 is applied to a printer 35 by way of the input-output controller (IOC) 24. The output data comprises the following representative list of parameters: analyzer identification, time and date of analysis, gross saturated BTU/CF, real specific gravity, Z factor, total area of GC output function peaks, names of each of the gas mixture components (methane, carbon dioxide, etc.) with each respective concentration to two decimal places (XX.XX%), peak retention times, response factors and other important analysis information.

Status control panel 22 is used during initial system start-up and during system repair procedures and comprises a switch light array 22 and a high speed paper tape reader 34. Application and diagnostic programs are applied to system 10 by way of a high speed paper tape reader 34. The switch light array 22 forms a control and status display to enable the operator to command and monitor the status of the system performance. Keyboard 38 provides an alphanumeric input capability for use by an operator for changing system constants, editing tabulated values, entering time-date data and performing other routine diagnostic functions. Console 38 also displays the data currently being sent to the printer 35 from processor 30.

I/O controller 24 comprises a plurality of programmable hardware which formats data 41 being transferred to and from the processor 30 with two analog outputs for remote transmission carrying BTU and specific gravity intelligence. An output line 24a and 41 of controller 24 is effective to drive and control the converter 18 to determine its operational sampling rate $r_o$. The sampling rate is varied as a function of the gas mixture undergoing analysis. Contained in the signal on line 24a are command and status words associated with an auto-ranging amplifier which permits proper processing of the broad dynamic range (5 micro-volts to 10 volts peak) of GC detector output 14a. Controller 24 also provides signals on lines 23a, 24b which drive the status panel indicator devices 22a and to operate the GC solenoids in GC 15 at the proper time and sequence. Controller 24 senses the state of the status control panel switches 22a and customer-provided contact closures 40. This switch data on lines 23a and 40a is communicated to the processor main operating program via an input port polling routine.

A stored application program resides in processor 30 after being read from paper tape 19 via a high speed paper tape reader 34. Processor 30, upon receiving the execute command from status control panel 22 sequentially executes the program instructions. The program directs the operation of the entire system by taking data from the sources interfacing the controller 24, issuing commands via the controller to the gas chromatograph 15, transferring data to the proper output device such as printer 35 and status panel indicators. A dialog is maintaining with the operator at keyboard console 38 is required. The machine code for a typical gas mixture program is enclosed as pages 1–21 for use on processor 30. This code is given in octal format with every eighth address location given by the left hand column in octal format.

Figure 3B:
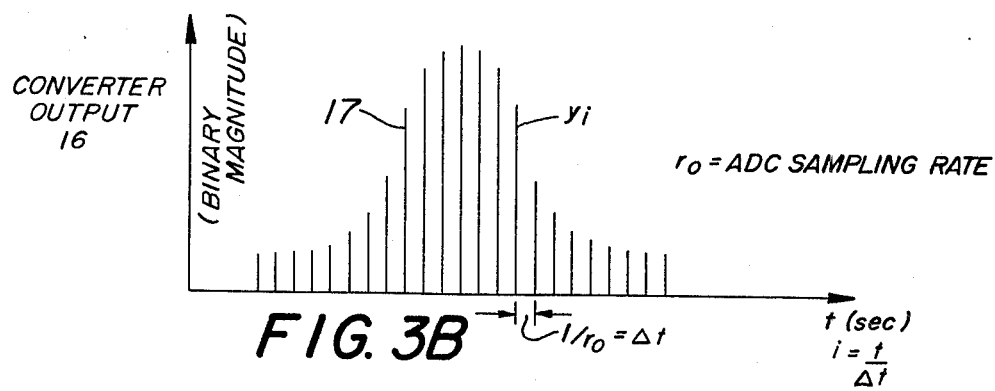

The purpose of the rate of change estimator 20 is to determine the rate of change (derivative) with respect to time of a sampled data signal 17 shown in FIG. 3B which is the digitized output of converter 18. Estimator 20 uses a minimum amount of computational components achieved by using a recursive digital feedback technique. In so doing, past time values of the estimated rate of change function are used to form the current estimated value of the same function.

Signal 14 is representative time-wise of the constituents of the unknown gas mixture on line 12. Signal 14 is a continuous, time-varying signal which is sampled at equally spaced time intervals ($\Delta t$) using A/D converter 18, FIG. 3C. The function of the A/D converter is to sample and digitize signal 14 and to present a stream of digital values to input of the rate of change estimator logic. The inverse of the sampling interval is the sampling rate or $r_o = 1/\Delta t$. The sampling rate $r_o$ is determined by the characteristics of the gas chromatograph analysis to be run.

Figure 3C:
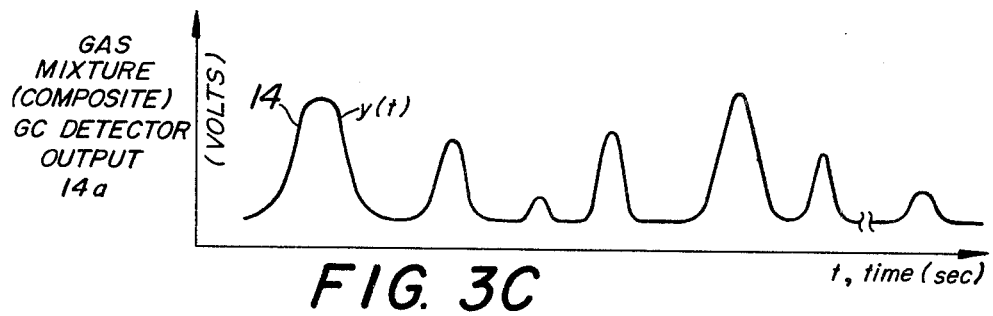

The rate of change function and the original signal are both delivered to processor 30 to undergo feature detection provided by subroutine in the program. The logic of this routine analyzes the GC detector output signal 14 and its associated derivative for the purpose of determination of the area underneath the peaks of the GC output curve as shown in FIG. 3C. Decisions on the following questions are made:

(1) Is the GC signal still at base line level?
(2) Has a chemical component begun to emerge?
(3) Has a maxima been reached?
(4) Has a decline begun?
(5) Has the declining component reached a base line?

Figure 4A:
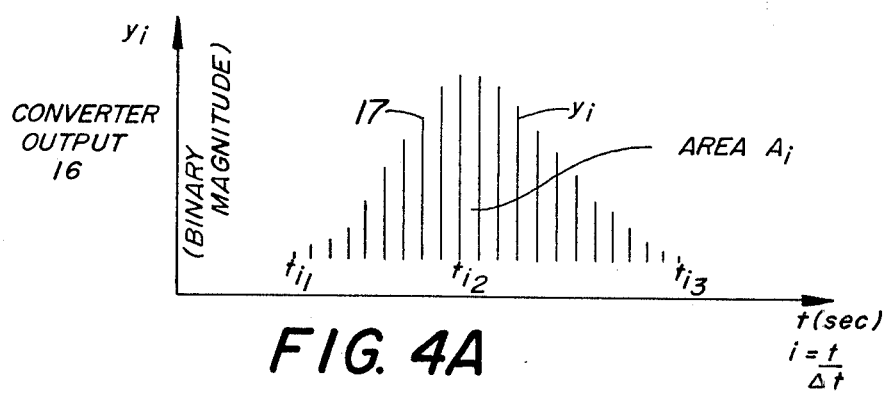
FIGS. 4A–B are waveforms of converter output and rate of change estimator system output helpful in explaining operation of FIGS. 1 and 2.
Figure 4B:
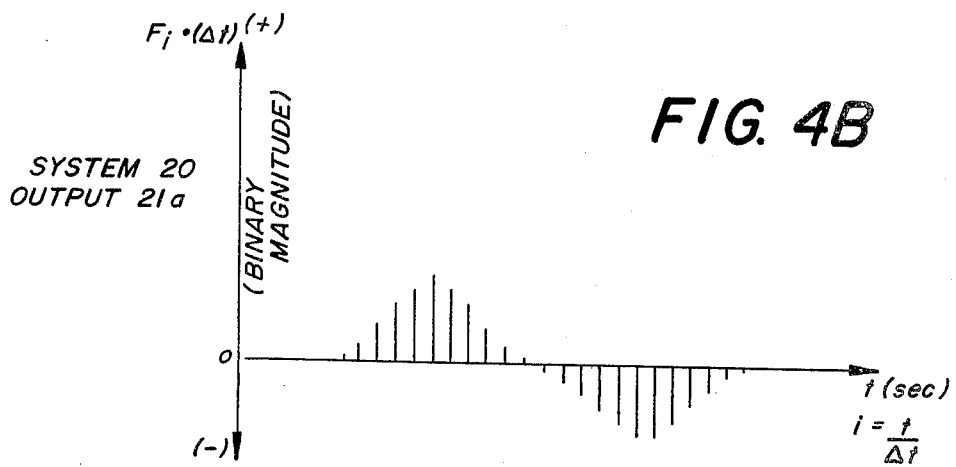

The answers to these questions determine the logic path taken and are used to control the computation of the area $A_i$ under the GC detector signal curve, FIG. 4A. The area under the curve $y_i$ begins at the first departure from base line and should end at the return to base line. This process is carried out continually in real time during the chemical analysis so that each of the emerging components is, in turn, recognized and integrated.

At the end of this analysis process, a list or table is available which contains the areas associated with each of the components. Next, each of these areas are corrected for any existing base line offset by applying a geometric algorithm. This algorithm assumes that the base line varies linearly with time. Given knowledge of the slope and a constant, the program then applies a trapezoidal correction. It is these corrected areas which are then used to compute the actual composition of the composite gas undergoing analysis.

The composition of the gas stream being tested is computed by applying "response factors" or "calibration factors." In principle, the percentage or relative amount of each component in the sample is proportional to the measured area under the GC detector output curve. In practice, some deviations from the theoretical percentage values are found and these are accounted for through the usage of these "calibration factors." Ideally, the calibration factors would be unity. The constituent areas are each multiplied by their respective calibration factor to arrive at the correct composition mix of the gas under analysis.

Next, the processing system utilizes the computed values of the percentages of the gas constituents to calculate the thermal heating value of the gas mixture. This can be done using a tabulated list stored in memory of the heating value contribution factors for each of the components. To perform this calculation, one must know the actual identity (chemical name) of each of the detected components. This identification process is performed by knowledge of the time of emergence for each gas constituent within the GC. Through experience a reliable history of emergence times has been accumulated and tabulated in the form of a look-up table stored in memory. Therefore, the stored program performs a matching process of the currently observed emergence times against the tabulated times. Knowledge of the chemical identity permits referencing of standard BTU contribution information for each constituent comprising the mixture. A computation of the weighted average is performed to arrive at the overall heating value of the mixture.

Similar computations are performed to arrive at the specific gravity or density of the mixture using the specific gravity contributions of each of the constituent components. Straightforward correction formulas are applied to arrive at the resulting BTU value and specific gravity. These corrections and adjustment techniques are published in American Gas Association Report AGA #3. The resulting BTU value, specific gravity value, and the list of percentages of each of the identified components of the gas mixture are considered the final output of the system which are then printed or displayed appropriately.

Effect of Noise on Rate of Change Estimator Performance

Most electronic systems suffer performance degradation in the presence of noise. Noise refers to any spurious disturbances that tend to obscure the signal being processed. Gas chromatograph systems are adversely affected by noise voltages since the amplitude of the GC detector output 14a can, in some analyses, be of the same order of magnitude as average system noise levels. However, the processing system must be able to distinguish between valid peaks and rapid changes in the GC detector output signal and random noise spikes in addition to other unwanted long term disturbance associated with base line drift.

Noise impulses have an inherently broad frequency content. Rate of change detection and computational logics similarly have response functions which are of the form of the following equation and therefore are highly sensitive to noise impulses.

$$E_{out} = j\omega \cdot E_{input} \text{ where } \omega = 2\pi f \tag{1}$$

In the case of operational amplifier differentiator devices, noise impulses cause rapid amplifier saturation states and subsequent long term "hang-up" conditions.

Examining the amplitude function of GC detector output signal 14, FIGS. 3C, 4A, the task of system 10 is to determine the area $A_i$ bounded by the function $y_i$ and an arbitrary base line. The base line is the central value of the residual system noise when the system is not actively processing a sample. This area is determined by knowledge of when the function commences its rise ($t_{i1}$), peaks ($t_{i2}$) and terminates its decline ($t_{i3}$), FIG. 4A. One method of performing this area determination involves accurate knowledge of the behavior of the derivative function $dy(t)/dt$. Hence, the need arises for a rate of change estimator circuit to determine this time derivative function in real time.

A performance trade-off exists in the design of a system which must respond to rapid signal variations in the presence of noise and yet avoid unwanted system response (as subsequent decisions) to rapid rates of change associated with noise impulses. The rate of change estimator logic must be sufficiently sensitive to detect small rates of signal change associated with gas components which propagate through the GC tubing in a longer time distributed manner. It is the time derivative function that permits detection of the emergence of various gas components traveling through the chromatograph 15. The chromatograph is essentially an instrument that has a baseline output which is punctuated by deviations from the baseline as shown in FIG. 3C. These deviations tend to be bell-shaped curves somewhat like the statistical normal curve of error. Measurement of the areas under the GC output function of ten peaks, for example, will indicate the proportional amounts of 10 constituents of the gas sample injected into the GC. Therefore, different gas components arrive at the GC detector at different times. System 10 is effective to individually compute the area under each of these bell-shaped deviations. Performing this computation is straightforward in principle. In practice, difficulties arise when calculating a derivative from real information because the effects of noise are amplified in the calculation. The derivative forming process is more sensitive to noise than to the original signal because of the higher rates of voltage change associated with noise pulses.

System 20 provides an effective solution to these problems caused by noise by employing a recursive technique. Recursive implies that the signal output (digital word) of a previous computation time is used as an input data word during the current computation time. The use of memory is therefore required to permit the computational logic to process prior (historical) values of the signal.

System 20—Theory of Operation

Figure 5A:
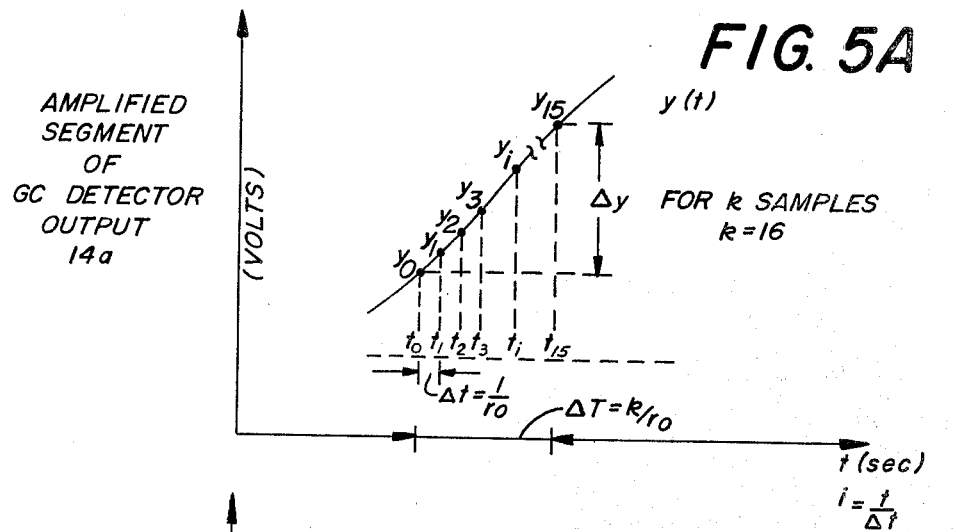
FIGS. 5A–B are amplified segments of the output of the gas chromatograph helpful in explaining the theory of operation with and without noise.
Figure 5B:
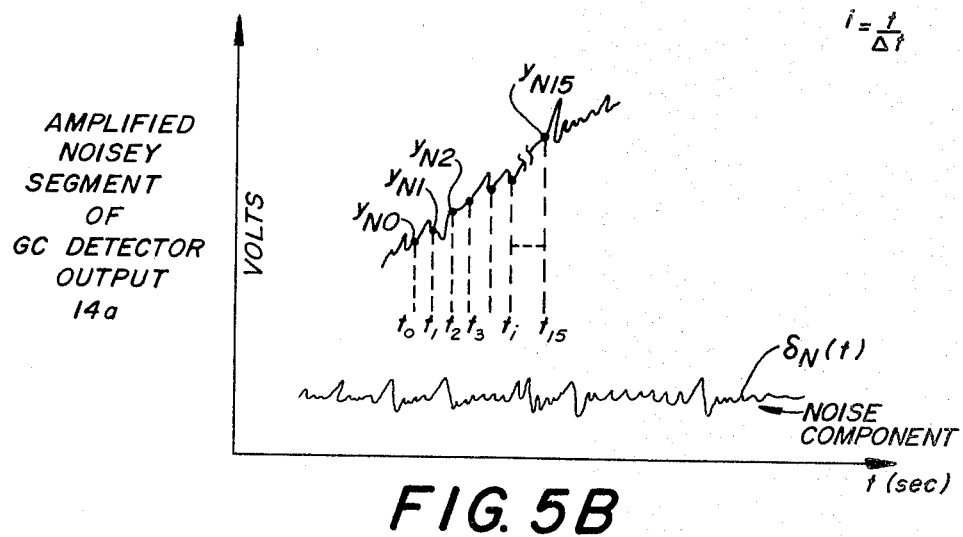

The function of the rate of change estimator system 20 is to determine the average rate of change of a noise-burdened signal $y(t)$ as shown in FIG. 5B. It may be assumed that the time elapsed between adjacent samples is $\Delta t$ and is constant for a specific application. Applying the simplest form of calculation to the waveform shown in FIG. 5A, we would take differences between successive values of $y(t)$ and call that an estimate of the derivative. Thus, in symbolic form:

$$\frac{\Delta y_i}{\Delta t} \propto \left[\frac{y_1 - y_o}{\Delta t}\right], \left[\frac{y_2 - y_1}{\Delta t}\right], \ldots \left[\frac{y_n - y_{n-1}}{\Delta t}\right] \tag{2}$$

The problem with this approach is its extreme susceptibility to noise as the sample time decreases. Extreme care is required in later processing if any useful results are to be achieved.

It can be seen that these values of the derivative would vary radically from one sample time to the next if noise impulses are considered:

$$\frac{\Delta y_i}{\Delta t} \propto \left[\left(\frac{y_i + \delta_{Ni}}{\Delta t}\right) - \left(\frac{y_{i-1} + \delta_{Ni-1}}{\Delta t}\right)\right] \tag{3}$$

where $\delta_{Ni}$ represents the instantaneous noise voltage to be instantaneously superimposed upon the GC detector output signal of FIG. 5A.

The process herein for forming the derivative employs signal amplitude averaging over a large time interval (larger quantity of samples) thereby cancelling short term noise deviations. Referring again to FIGS. 5A and 5B, $y(t)$ depicts a small segment of a GC peak waveform or curve and is shown to be noise free, smooth and continuous. Let k represent an extended number of sample times. If k=16, the rate of change estimator 20 will be programmed to use a 16 point computational sequence. To form the estimated derivative, we take the signal amplitude ($y_o$) at the beginning of a 16 sample intervals and subtract it from the next 15 successive amplitude values of $y(t)$, and then sum these differences.

$$\frac{\Delta y}{\Delta t} \text{ (avg)} \propto \left(\frac{y_1 - y_o}{\Delta t}\right) + \left(\frac{y_2 - y_o}{\Delta t}\right) + \left(\frac{y_3 - y_o}{\Delta t}\right) + \ldots \left(\frac{y_{15} - y_o}{\Delta t}\right) \tag{4}$$

Note that $\Delta y/\Delta t$ (avg) is proportional to the average rate of change of $y(t)$ during the period defined by $k\Delta t$ seconds. Thus, we are performing a differentiation process by doing an integration or summation process.

Examining FIG. 5B, it can be seen that when the noise function $\delta_N(t)$ is superimposed upon $y(t)$, it will be additive to some of the samples and subtractive from others. It is found that the noise voltage will be cancelled out over a sufficiently long time interval. Thus, by adding the computed differences over an extended time period, an advantage of cancelling out the noise function $\delta_N(t)$ occurs. However, the objective of determining the average rate of change has been met.

System 20 uses a recursive technique which is substantially equivalent to the process defined by equation 4. Certain precautions must be observed to avoid possible round-off error in the logic circuit. Both techniques (equation 4 and 5) can be shown to provide the same numerical rate of change magnitude. The advantage of the recursive technique is that much less circuitry is required for implementation and execution is faster. In the prior example using 16 samples, it was required to perform 15 subtractions and additions. In a real time processing system, this plurality of operations could possibly prevent the system from keeping abreast with the total computational task. Hence, the recursive technique disclosed is much more efficient than the basic definition of the process defined by equation 4.

$$F_{i'}(\Delta t) = F_{i-i'}(\Delta t) + y_{i+k} - y_i - k(y_i - y_{i-l}) \quad (5)$$

where
$F_i$ = estimate of the average rate of change of the input signal
i = time indexing parameter (i = 1,2,3, ... n), (ith instant)
y = amplitude of input signal
k = sampling parameter System 20 delays the input signal such that it can compute using several values available to it simultaneously. This delay function is performed using shift register techniques. The parameter k is used directly in equation 5 as a multiplier which permits adjustment of the behavior of the system 20. By increasing k, a larger sample quantity may be used and system 20 rejects larger amounts of high frequency noise components. In practice, the parameter k is adjusted for a specific GC application.

Figure 2:
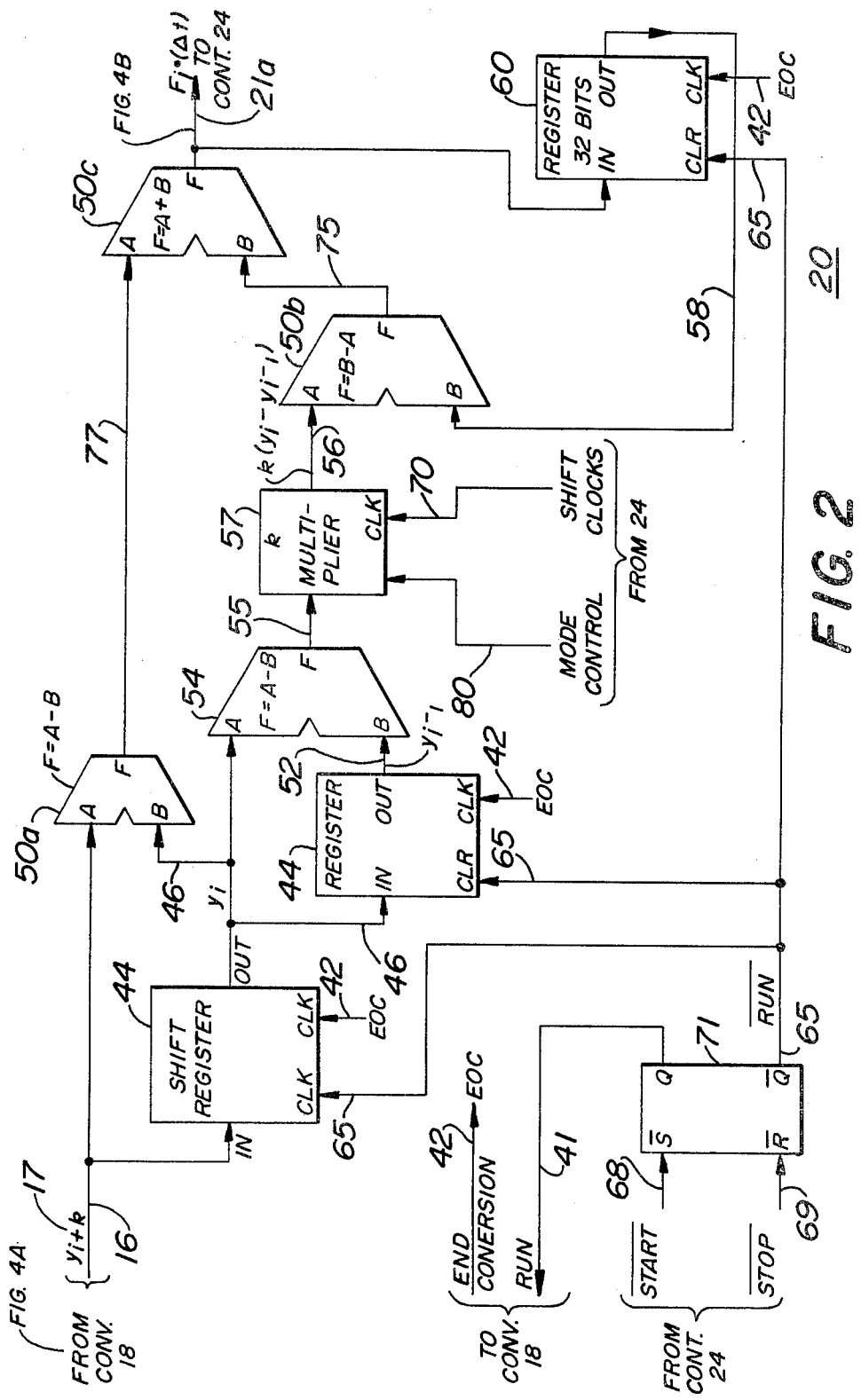
FIG. 2 is a block diagram of the rate of change estimator system of FIG. 1.

Referring now to FIG. 2, in system 20, an arbitrary binary word 17 given by $y_{i+k}$ represents an output data word of 32 bit length from the A/D converter 18, FIG. 1. This data word is one of a series of data words shown in FIG. 4A. Upon receiving a start command (bar indicates active low logic levels) on line 68, the Q output 41 of RS flip-flop 71 goes active high (RUN) and is used to command the converter 18 to commence the conversion process. The $\overline{Q}$ output of flip-flop 71 resets the first stage of a shift register array 44 and 32 bit latch registers 44 and 60. Prior to the arrival of the end of conversion signal 42 from converter 18, a stop command on line 69 is sent from controller 24 thereby placing the Q,$\overline{Q}$ outputs 41 and 65 of flip-flop 71 in the inactive state. Upon arrival of the end of conversion status signal 42 from converter 18, the data sample currently being sent from converter 18 is clocked into shift register array 44. Latch registers 44 and 60 are similarly strobed by signal 42 to store the data words present on their respective input lines. Shift register array 44 comprises a bank of flip-flops forming a 32 times k array of 1 bit storage elements. The function of this array is to deliver the data sample $y_i$ on line 46 which occurred k samples ago in the past, the $y_{i+k}$ signal on line 16. Hence, array 44 is a form of digital delay device which can be programmed to achieve k $\Delta t$ units of time delay.

Shift register array 44 delivers signal $y_i$ on line 46 to a digital subtractor device 50a. Device 50a performs a subtraction operation F = A - B to yield the signal $(y_{i+k} - y_i)$ on line 77. Each element of device 50a processes a 4 bit slice of each of the two 32 bit words $y_{i+k}$, $y_i$ currently existing on the inputs A and B. A similar subtractor device 54 forms the term $y_i - y_{i-l}$ on line 55. The term $y_{i-l}$ on line 52 is formed using a 32 bit latch register whose function is to provide a storage delay of 1 sample time, $\Delta t$.

The term $(y_i - y_{i-l})$ is now applied to the input of the k multiplier 57 where k has been assumed to be set at a value 16. The signal on line 55 is strobed into the lower 32 bit positions of the 40 bit shift register 57 comprised of five 8 bit shift registers. Thereafter, the data word $y_i - y_{i-l}$ is shifted 4 bit places towards the most significant bit end of the shift register 57 thereby accomplishing a multiplication operation of $2^4$ or 16. The series of shift clock pulses 70 and input/output mode control signals 80 to device 57 are developed by and sent from logic contained in the controller 24 to yield at the appropriate time on line 56 the signal $k(y_i - y_{i-l})$. This signal is then applied to the A input of device 50b which performs the subtraction function F = B - A. The variable k is related to the quantity of samples which are necessary and sufficient to adequately remove the noise component $\delta(t)$. The parameter k is shown to be set at 16 but in practice could be a smaller or larger integer depending upon the severity of the noise voltage swings. Hence, the k multiplier device 57 could take the form of a programmable arithmetic logic unit. If k were programmable, then shift register array 44 would also be comprised of additional logic gates to provide an associated reconfiguration so as to always achieve a delay of k $\Delta t$ sample times.

The signal $F_{i'}(\Delta t)$ on line 21a is applied to a 32 bit wide latch register 60 similar to latch register 44. Device 60 is similarly cleared and clocked with the signals 65 and 42 respectively thereby providing a single sample time delay and consequently the signal $F_{i-l}(\Delta t)$ on line 58. Line 58 supplies the "B" data inputs to the previously discussed subtractor 50b. Device 50b is identical to devices 50a, 54, and 50c but is programmed to provide the arithmetic function F = B - A on line 78. Given the input terms as shown on wires 56 and 58, device 50b develops an output signal $F_{i-l}(\Delta t) - k(y_i - y_{i-l})$ on line 75 which is applied to the B input of adder device 50c. Device 50c provides the arithmetic function F = A + B thereby yielding at its output the function $F_{i'}(\Delta t)$, the estimation of the time derivative of the GC detector output.

It will be understood that the signal $F_{i-l}$ on line 58 represents the prior (one sample time) estimate of the time derivative and this term is utilized to form the current estimate of the rate of change. The signal on line 21a lags input function 17 on line 16 by a period of k sample times.

While particular embodiments of the invention have been shown and described, this is not to be considered as necessarily limiting of the invention, it being understood that numerous changes may be made within the scope of the invention to suit the technical requirements of particular applications. For example, it will be understood that system 20 may be implemented in the form of a program by processor 30. Further, in an analog form of system 10, instead of an A/D converter 18, an analog sample may be provided by a sample and hold circuit, for example, and estimator system 20 may be designed as an analog system with processing as desired. Still further in the analog form, signal 14 may be taken without sampling and estimator system 20 would estimate in analog form on a continuous basis. The analog output of system 20 may then be sampled as desired in accordance with the processing being used.

TABLE OF COMPONENTS

In systems 10 and 20, the following components provide the operation and function herein described.

| Reference Character | Component | Type |
|---|---|---|
| 15 | gas chromatograph | EAI 85.0001 (PR-250) Electronic Associates, Inc. |
| 18 | A/D converter | EAI 22.1311 & 40.0788-1 |
| 22 | status control panel | EAT 20.1348 |
| 24 | I/O controller | EAI 2214 1172, 22.1228-3 40.0792-7, 22.1233 |
| 30 | processor | EAI Datapacer 46.0221 |
| 44 | shift register | 74 164 (64x) |

TABLE OF COMPONENTS-continued

In systems 10 and 20, the following components provide the operation and function herein described.

| Reference Character | Component | Type |
| --- | --- | --- |
| 48,60 | register | 74 273 (4x) |
| 50a-c, 54 | adder/subtractor | 74S381 (8x) |
| 57 | multiplier | 74S299 (5x) |

What is claimed is:

1. A system for measuring and analyzing a gas mixture comprising
    gas processing means for producing a time varying signal related to the constituents of the gas mixture,
    means for sampling and converting to digital form said time varying signal thereby to provide a sampled data signal, and
    digital estimator means for providing a rate of change estimate signal with respect to time of said sampled data signal, said digital estimator means including (1) recursive digital feedback means coupled to an output of said digital estimator means for producing at least one past time value signal of the estimated rate of change signal and (2) feed forward means coupled to the sampling means for producing at least one other past time value signal of the sampled data signal, means for combining both past time value signals with the sampled data signal for producing a signal area defined for an interval and above the amplitude of one of said past time value signals thereby providing the estimated rate of change signal.

2. The system of claim 1 in which said sampling means includes means for providing said sampled data signal whose amplitude is a function of the gas constituents.

3. The system of claim 1 in which said sampling means includes means for sampling said time varying signal at equally spaced time intervals to provide said sampled data signal in the form of a series of equally spaced amplitude dependent digital signals.

4. The system of claims 1, 2 or 3 in which said feed forward means includes means for delaying the sampled data signal from said sampling means by a predetermined number of sample times thereby to produce a delayed sampled data signal as the other past time value signal.

5. The system of claim 4 in which said feed forward means includes means for further delaying said delayed sampled data signal, and means for producing the difference between said delayed sampled data signal and said further delayed sampled data signal and for multiplying the resultant signal by said predetermined number of sample times to produce a multiplied difference signal.

6. The system of claim 5 in which said recursive feedback means includes further means for delaying the rate of change estimate signal to provide a delayed rate of change estimate signal delayed by one time interval, and further means for combining said delayed rate of change estimate signal and said multiplied difference signal for producing a recursive past time value signal.

7. The system of claim 6 in which said combining means includes means for combining said recursive past time value signal and said delayed sampled data signal with the sampled data signal for producing said estimated rate of change signal.

8. The system of claim 4 in which there is provided processing means for performing analysis of said rate of change estimate signal to provide the composition of the constituents of the gas mixture.

9. A system for gas measurement and analysis comprising
    gas processing means for producing a time varying signal related to the gas,
    means for sampling said time varying signal thereby to provide a sampled data signal, and
    estimator means for providing a rate of change estimate value with respect to time of said sampled data signal, said estimator means including (1) means for recursively feeding back an output of said estimator means for producing at least one past time value of the estimated rate of change value and (2) means for feeding forward an output of said sampling means for producing at least one other past time value of the sampled data signal, means for combining both past time values with the sampled data signal for producing a signal area defined for an interval and above the amplitude of one of said past time value signals thereby providing the estimated rate of change value.

10. The gas measurement and analysis system of claim 9 in which said sampling means includes means for converting said time varying signal to digital form thereby to provide said sampled data signal in digital form.

11. The gas measurement and analysis system of claim 10 in which said sampling means includes means for sampling said time varying signal at equally spaced time intervals to provide said sampled data signal in the form of a series of equally spaced amplitude dependent digital signals.

12. The gas measurement and analysis system of claims 10, 11 or 9 in which said feeding forward means includes means for delaying the sampled data signal from said sampling means by a predetermined number of sample times thereby to produce a delayed sampled data value.

13. The gas measurement and analysis system of claim 12 in which said feeding forward means includes means for further delaying said delayed sampled data value and means for producing the difference between said delayed sampled data value and said further delayed sampled data value and for multiplying the resultant value by said predetermined number of sample times to produce a multiplied difference value.

14. The gas measurement and analysis system of claim 13 in which said recursive feedback means includes further means for delaying the rate of change estimate value to provide a delayed rate of change estimate value delayed by one time interval, and further means for combining said delayed rate of change estimate value and said multiplied difference value for producing a recursive past time value.

15. The gas measurement and analysis system of claim 14 in which said combining means includes means for combining said recursive past time value and said delayed sampled data value with the sampled data signal for producing said estimated rate of change value.

* * * * *